United States Patent
Torres et al.

(10) Patent No.: US 11,986,588 B2
(45) Date of Patent: May 21, 2024

(54) ELECTRONIC SYSTEM

(71) Applicant: Presspart GmbH & Co. KG, Marsberg (DE)

(72) Inventors: Victor Torres, Barcelona (ES); Benjamin Jung, Pulheim (DE)

(73) Assignee: Presspart GmbH &Co. KG, Marsberg (DE)

( * ) Notice: Subject to any disclaimer, the term of this patent is extended or adjusted under 35 U.S.C. 154(b) by 689 days.

(21) Appl. No.: 17/082,417

(22) Filed: Oct. 28, 2020

(65) Prior Publication Data
US 2021/0138168 A1     May 13, 2021

(30) Foreign Application Priority Data

Nov. 13, 2019 (EP) .................................... 19208782

(51) Int. Cl.
*A61M 15/00* (2006.01)
*H04Q 9/00* (2006.01)

(52) U.S. Cl.
CPC .... *A61M 15/0068* (2014.02); *A61M 15/0021* (2014.02); *A61M 15/009* (2013.01);
(Continued)

(58) Field of Classification Search
CPC .............. A61M 15/00; A61M 15/0068; A61M 15/002; A61M 15/0021; A61M 15/009; A61M 2205/3334; A61M 2205/3553; A61M 2205/3584; A61M 2205/581–583; A61M 2205/3592; A61M 11/0002;
(Continued)

(56) References Cited

U.S. PATENT DOCUMENTS

2003/0168057 A1 * 9/2003 Snyder ................ A61M 15/002
    128/200.11
2007/0125370 A1 * 6/2007 Denyer ............. A61M 15/0085
    128/200.14

(Continued)

FOREIGN PATENT DOCUMENTS

| EP | 3363485 A1 | 8/2018 |
|---|---|---|
| EP | 3485930 A1 | 5/2019 |

OTHER PUBLICATIONS

European communication dated May 29, 2020 in corresponding European patent application No. 19208782.3.

*Primary Examiner* — Annette Dixon
(74) *Attorney, Agent, or Firm* — NIELDS, LEMACK & FRAME, LLC

(57) ABSTRACT

Electronic system including an inhaler device for dispensing a medicament formulation in aerosol or dry powder form and an external device which is configured to receive data communicated from the inhaler device. The inhaler device includes a mouthpiece and a flow rate sensor for sensing a flow rate of an inhalation flow which is caused by a patient upon inhalation through the mouthpiece and in which the medicament formulation is entrained or dispensed. The inhaler device further comprises an actuation sensing device having at least one actuation sensor which is configured to sense preparatory steps of the inhaler device in order to prepare a use of the inhaler device and/or to sense the actuation of the inhaler device in order to dispense the medicament formulation. The actuation sensor and the flow rate sensor are configured to generate sensor signals.

17 Claims, 2 Drawing Sheets

(52) U.S. Cl.
CPC ......... *H04Q 9/00* (2013.01); *A61M 2202/064* (2013.01); *A61M 2205/3334* (2013.01); *A61M 2205/3584* (2013.01); *A61M 2205/581* (2013.01); *A61M 2205/582* (2013.01); *A61M 2205/583* (2013.01); *H04Q 2209/40* (2013.01)

(58) Field of Classification Search
CPC .... A61M 11/02; A61M 11/04; A61M 11/041; A61M 11/042; A61M 11/06; A61M 15/0001; A61M 15/0003; A61M 15/0013; A61M 15/0015; A61M 15/0016; A61M 15/0028; A61M 15/003; A61M 15/0045; A61M 15/005; A61M 15/0051; A61M 15/0065; A61M 15/0066; A61M 15/008; A61M 15/0085; A61M 15/0086; A61M 15/0091; A61M 15/06; A61M 15/08; A61M 15/085; A61M 16/006; A61M 16/0009; A61M 16/0051; A61M 16/0066; A61M 16/021; A61M 16/024; A61M 16/06; A61M 16/0638; A61M 16/0655; A61M 16/0683; A61M 16/0688; A61M 16/0816; A61M 16/1055; A61M 16/106; A61M 16/1065; A61M 16/107; A61M 16/14; A61M 16/16; A61M 16/20; A61M 16/201; A61M 16/204; A61M 16/208; A61M 16/209; A61M 2015/002; A61M 2015/008; A61M 2016/0015; A61M 2016/0021; A61M 2016/0027; A61M 16/003; A61M 2016/0039; A61M 2016/0042; A61M 2202/04; A61M 2202/064; A61M 2205/0216; A61M 2205/0233; A61M 2205/07; A61M 2205/18; A61M 2205/273; A61M 2205/276; A61M 2205/3303; A61M 2205/3313; A61M 2205/3317; A61M 2205/332; A61M 2205/3331; A61M 2205/3368; A61M 2205/3375; A61M 2205/3561; A61M 2205/3569; A61M 2205/36; A61M 2205/43; A61M 2205/44; A61M 2205/50; A61M 2205/502; A61M 2205/505; A61M 2205/52; A61M 2205/582; A61M 2205/583; A61M 2205/584; A61M 2205/70; A61M 2205/75; A61M 2205/7545; A61M 2205/8206; A61M 2206/11; A61M 2206/14; A61M 2206/18; A61M 2210/0618; A61M 2210/0625; A61M 2230/005; A61M 2230/06; A61M 2230/205; A61M 2230/30; A61M 2230/40; A61M 2230/42; A61M 2230/50; A61M 2230/60; A61M 2230/63; A61M 2230/65; H04Q 9/00; H04Q 2209/40; G16H 10/60; G16H 20/13; G16H 20/10; G16H 20/40; G16H 40/67; A24F 40/42; A24F 47/008; A61B 2560/0242; A61B 2560/0276; A61B 2560/028; A61B 2560/0462; A61B 2562/0247; A61B 5/0022; A61B 5/087; A61B 5/0871; A61B 5/091; A61B 5/097; A61B 5/1112; A61B 5/4833; A61B 5/4839; A61B 5/4848; A61B 5/486; A61B 5/742; A61B 5/746; A61F 5/08; A61F 5/56; A61K 31/05; A61K 31/352; A61K 31/465; A61K 36/185; A61K 36/81; A61K 9/0019; A61K 9/0053; A61K 9/006; A61K 9/007; A61K 9/0073; A61P 1/00; A61P 1/04; A61P 1/08; A61P 1/14; A61P 11/00; A61P 11/06; A61P 13/10; A61P 15/00; A61P 17/02; A61P 17/04; A61P 19/02; A61P 21/00; A61P 25/00; A61P 25/04; A61P 25/08; A61P 25/14; A61P 25/16; A61P 25/18; A61P 25/20; A61P 25/22; A61P 25/24; A61P 25/30; A61P 25/32; A61P 27/06; A61P 29/00; A61P 31/04; A61P 31/14; A61P 31/18; A61P 35/00; A61P 35/02; A61P 9/10; A61P 9/12; A62B 18/10; A62B 23/06; A62B 23/18; B23H 1/00; B23H 11/00; B23H 7/20; B23Q 17/20; B66B 13/24; B66B 13/30; B66B 13/301; B66B 13/303; G01F 1/22; G01F 1/40; G05B 19/401; G05B 19/408; G05B 19/4097; G05B 19/425; G05D 7/012; H05B 1/0244; H05B 1/025; H05B 2203/016; H05B 2203/021; H05B 2203/022; H05B 3/04; H05B 3/265; H05B 3/34; Y02P 3/34; Y02P 90/02; Y10T 137/7847; Y10T 137/7848

See application file for complete search history.

(56) References Cited

U.S. PATENT DOCUMENTS

| | | | |
|---|---|---|---|
| 2008/0078382 A1* | 4/2008 | LeMahieu | A61M 16/0069 128/200.24 |
| 2016/0144141 A1* | 5/2016 | Biswas | A61M 15/009 128/200.23 |
| 2016/0325058 A1* | 11/2016 | Samson | A61B 5/0022 |
| 2017/0119981 A1* | 5/2017 | Davidson | A61K 31/352 |

* cited by examiner

ELECTRONIC SYSTEM

TECHNICAL FIELD

The present invention relates to an electronic system comprising an inhaler device for dispensing a medicament formulation in aerosol or dry powder form and an external device which is configured to receive data communicated from the inhaler device. The inhaler device comprises a mouthpiece and a flow rate sensor for sensing a flow rate of an inhalation flow which is caused by a patient upon inhalation through the mouthpiece. The medicament formulation is entrained or dispensed into the inhalation flow. The inhaler device further comprises an actuation sensor which is configured to sense preparatory steps of the inhaler device in order to prepare a use of the inhaler device and/or to sense the actuation of the inhaler device in order to dispense the medicament formulation. The actuation sensor and the flow rate sensor are configured to generate sensor signals. The inhaler device further comprises a wireless transmitting unit for communicating data related to the sensor signals to the external device. The electronic system further comprises an instruction unit configured to generate visual, tactile and/or acoustic instructions in order to support the patient during use of the inhaler device and an evaluation unit for evaluating the sensor signals and/or the communicated data. The evaluation unit is configured to evaluate the use of the inhaler device by comparing measurements taken by the sensors with the instructions given to the patient and/or with predefined data.

BACKGROUND OF THE INVENTION

Inhaler devices such as inhalers are commonly used to deliver drugs into the lung of a patient in need thereof. Different types of inhalers have been developed and are available on the market, amongst which dry powder inhalers (DPIs), metered dose inhalers (MDIs) and soft mist inhalers are attractive in the treatment of various respiratory problems such as asthma, bronchitis or chronic obstructive pulmonary disease (COPD).

Metered dose inhalers (MDIs) are medication delivery devices which deliver a pharmaceutical active formulation including one or another pharmaceutical active compounds to a human or another mammalian patient. Typically, the pharmaceutical formulation is delivered by the MDIs in unit doses in form of an aerosol. Each actuation of the MDIs delivers one unit dose. The unit dose is expelled by the MDIs and is taken into the body of the patient on inhalation, via the nose or mouth. The pharmaceutical formulation is delivered to or via the respiratory tract, notably to the lungs of the patient on inhalation. Metered dose inhalers are typically used for the treatment of respiratory infections and disorders including respiratory tract infections, obstructive lung disease, inflammatory lung disease and chronic obstructive pulmonary disease. Asthma treatment is a particularly common use of MDIs.

Studies have shown that the effect of an inhaled pharmaceutical formulation is heavily dependent on, amongst others, the ability of the patient to comply with a prescribed treatment regimen which has been for example defined by a physician. The prescribed treatment regimen in particular aims at the patient to inhale the right amount of the pharmaceutical formulation. It has been found that a lot of patients living with asthma do not use their inhaler adequately and thus do not receive the correct amount of medication upon inhalation. In particular, lack of hand-breath coordination (press and breathe), an incorrect speed and/or depth of inhalation, an incorrect actuation of the container and a missing breath-hold after inhalation of the dose of medicament are the most frequent errors when using an MDI. Thus, there is a need to implement guiding functions in the metered dose inhaler in order to help patients to adequately use their inhaler.

EP 3 485 930 A1 discloses an inhalation system comprising a metered dose inhaler for dispensing an aerosol dose during use and a separate computing device such as a smart phone for computing signals received from the metered dose inhaler. The metered dose inhaler comprises an electronic dose counter and a flow rate sensor. Moreover, the inhaler comprises a transmitting unit for transmitting signals of the electronic dose counter as well as of the flow rate sensor to the computing device. The computing device is configured to generate visual and/or acoustic messages independently of the electronic dose counter and the flow rate sensor in order to guide the patient through multiple steps of the use of the metered dose inhaler. The computing device is further configured to evaluate the use of the metered dose inhaler by comparing the transmitted signals of the electronic dose counter and the flow rate sensor with the visual and/or acoustic messages. The messages outputted by the computing device stay the same no matter whether the patient uses the inhaler according to the instructions or not.

It is an object of the present invention to provide an electronic system which improves the use of an inhaler device by the patient such that compliance with a prescribed treatment regimen can be easier and more rapidly achieved.

SUMMARY OF THE INVENTION

This object is archived by an electronic system comprising the features of claim 1. Preferred embodiments are set out in the dependent claims.

According to the present invention, the evaluation unit is further configured to autonomously adapt the timing and/or the content of the instructions in order to ensure that the measurements taken by the sensors correspond to a use of the inhaler device by the patient according to the predefined data. The evaluation unit is further configured to verify whether the adaptation of the timing and/or the content of the instructions leads to a use of the inhaler device by the patient according to the predefined data during a subsequent use of the inhaler device by comparing measurements taken by the sensors during the subsequent use of the inhaler device with the predefined data. The evaluation unit is further configured to evaluate how single adaptations of the instructions in timing and/or content impact on the individual use of the inhaler device by the patient by comparing measurements taken by the sensors during the subsequent use of the inhaler device with measurements taken from the sensor during the previous use of the inhaler device.

Preferably, the predefined data is specific for the individual patient. Optionally, the predefined data has been individually defined for each patient by a physician taking into account amongst others the severity of the disease of the patient as well as the constitution of the patient.

In case, for example, the duration of inhalation by the patient during use of the inhaler device is shorter than the duration defined by the predefined data, the evaluation unit may in a subsequent use adapt the content of the instructions in order to instruct the patient to increase the duration of inhalation. For example the evaluation unit may adapt the content of the instructions such that the instruction unit outputs the instruction: "Inhale longer". Alternatively or additionally, the evaluation unit may adapt the timing of the instructions in a subsequent use of the inhaler device such that the instructions to start inhalation are outputted to the patient by the instruction unit at an earlier point of time compared to the previous use of the inhaler device. In doing so the inhaler advantageously adapts to the inhalation behavior of the patient. Thus, the proper use of the inhaler, namely in correspondence with the predefined data, is achieved more rapidly compared to the use of a conventional inhaler not being able to adapt the instructions in content and time. The visual, tactile and/or acoustic instructions may be outputted by the instruction unit via a display, a vibration unit and/or speakers. The speakers, the vibration unit and/or the display may be arranged on the inhaler device or the external device.

The comparison of measurements taken by the sensors during the subsequent use of the inhaler device under use of the adapted instructions with the predefined data allows the determination whether the optimal use of the inhaler device according to the predefined data has been achieved.

By comparing measurements taken by the sensors during the subsequent use of the inhaler device with measurements taken from the sensors during the previous use of the inhaler device the evaluation unit is configured to evaluate the impact of each of the adaptations of instructions to the use of the inhaler device. Data relating to the impact may be stored in a database of the electronic system. The database may be stored on the inhaler device or the external device.

In an embodiment of the present invention the evaluation unit is further configured to consider the impact of adaptations of the instructions in timing and/or content on the individual use of the inhaler device when autonomously adapting the timing and/or the instructions. Preferably, an algorithm of artificial intelligence (AI) is used to value the impact of each adaptation of the instructions and to consider this impact when autonomously adapting the time and/or the content of the instructions. In doing so the time needed to manage the patient to use the inhaler in compliance with the predefined data is shortened compared to the use of conventional inhalers not being able to adapt the content and the timing of the instructions.

Optionally, the evaluation unit may also consider patient specific data from various sources when autonomously adapting the timing and/or the instructions. Such patient specific data may be for example spirometry data, 3D models of airways based on a CT scans, flow rate characteristics when using the inhaler device and wheezing patterns of the patient. The data may be gathered during a physical examination of the patient and may be stored on a server of the electronic system, the server being accessible by the evaluation unit.

In another embodiment of the present invention the evaluation unit is further configured to evaluate how single adaptations to the instructions in timing and/or content impact on the use of the inhaler device based on an evaluation of data generated by further patients using other inhaler devices and to consider the impact on the use of the inhaler device when autonomously adapting the timing and/or the content of the instructions. Preferably, the data generated by further patients using other inhaler devices relates to inhaler devices of the same type and model as the inhaler device which is to be adapted to the inhalation behavior of the patient. The data generated by further patients using other inhalers may be stored on a server which may be accessible by the evaluation unit. Preferably, a database may be stored on the server in which the single adaptations, their impacts as well as the inhaler type may be stored. The evaluation of data generated by further patients and their consideration when adapting the instructions may be in particular used during the first uses of an inhaler device by a patient when the electronic system has not yet been able to evaluate any impacts of adaptations of the instructions on the individual use of the inhaler device by the patient.

Preferably, the predefined data comprises data relating to the duration of inhalation by the patient, the flow rate of the inhalation flow, the timing of an actuation, in particular a depression, of an aerosol container of the inhaler device, the time difference between the start of the inhalation flow upon inhalation by the patient and the actuation of the aerosol container and/or the duration of a depression of an aerosol container. As mentioned above, the predefined data may be individually defined by a physician for each patient depending amongst others on the severity of the disease and the constitution of the patient. The predefined data may also include an amount of a medicament which is desired to be taken into the lungs of the patient.

In an embodiment of the present invention the inhaler device comprises a mechanism for adapting a flow cross-section of the inhalation flow and/or a flow cross-section of a dispensing channel of the inhaler device through which the medicament formulation is dispensed into the inhalation flow. By adapting the cross-section of the inhalation flow the inhalation flow resistance may be changed during inhalation of the patient or between subsequent uses of the inhaler device. Moreover, by adapting the cross-section of a dispensing channel of the inhaler device properties of a stream of the medicament being dispensed through a valve from the aerosol container upon depression may be influenced. For example these properties may include the speed of the stream of medicament.

In another embodiment of the present invention the mechanism is formed as a movable flap which is configured to increase or decrease the flow cross-section of the inhalation flow. Preferably, the inhaler body comprises a top cover covering a first open end of the inhaler body through which the aerosol container is received and enclosing an upper end of the aerosol container. The inhaler body may comprise a separate air inlet duct through which air is drawn into the inhaler body upon inhalation by the patient. A flap may be mounted within the air inlet duct in order to change the flow cross-section of the inhalation flow.

Preferably, the mechanism is formed as multiple segments positioned transversally to a longitudinal axis of the dispensing channel and being configured to be driven inward into or outward of the dispensing channel in order to decrease or increase the flow cross-section of the dispensing channel. Preferably, the dispensing channel is a channel located in a nozzle block of the inhaler device. Preferably, the dispensing channel extends from a sump of the nozzle block to the dispensing nozzle of the nozzle block. The nozzle block may be located at a bottom portion of the inhaler body.

In an embodiment of the present invention the evaluation unit is further configured to control the mechanism of the inhaler device. Advantageously, the evaluation unit is not only configured to adapt the instructions but also to adapt the mechanism of the inhaler device. This allows multiple adjustment possibilities in order to improve the use of the inhaler by the patient on order to achieve compliance with predefined data.

In another embodiment of the present invention the evaluation unit is further configured to evaluate the use of the inhaler device by comparing the measurements taken by the sensors regarding their timing with the instructions given to the patient regarding their timing and/or predefined data. Comparing the timing of the measurements with the timing of the instructions is an easy and efficient way to detect the reaction time needed by the patient in order to react to the given instructions. Preferably, in case the reaction time of the patient is too long the evaluation unit may output the instructions at an earlier point of time considering the reaction time of the patient.

Preferably, the inhaler device is a metered dose inhaler, a dry powder inhaler or a soft mist inhaler. The present invention may be used in combination with any of the types of inhaler chosen from the group consisting of metered dose inhalers, dry powder inhalers or soft mist inhalers. The general function of a metered dose inhaler is for example described in document EP 3 363 485 which is herewith incorporated with reference in its entirety.

In an embodiment of the present invention the external device comprises the evaluation unit or is connectable thereto. The external device may be a smart phone, a hand held device or any other computational device such as a laptop.

In another embodiment of the present invention the electronic system comprises a server which is wirelessly accessible by the inhaler device and/or the external device and on which the evaluation unit is stored. The server may be wirelessly accessible via a mobile communication network, a wireless network or via a cabled network.

The above object is also achieved by a method for controlling an electronic system comprising the features of claim 13. According to the present invention the method comprises the steps of:
- providing an electronic system as described above,
- evaluating the use of the inhaler device by comparing measurements taken by the sensors with the instructions given to the patient and/or with predefined data,
- autonomously adapting the timing and/or the content of the instruction in order to ensure that the measurements taken by the sensors correspond to a use of an inhaler device by the patient according to the predefined data,
- verifying whether the adaptation of the timing and/or the content of the instructions leads to a use of the inhaler device by the patient according to the predefined data during a subsequent use of the inhaler device by comparing measurements taken by the sensors during the subsequent use of the inhaler device with the predefined data and
- evaluating how single adaptations of the instructions in timing and/or content impact on the individual use of the inhaler device by the patient by comparing measurements taken by the sensors during the subsequent use of the inhaler device with measurements taken from the sensors during the previous use of the inhaler device.

Advantageously the inhaler device adapts to the inhalation behavior of the patient in order to achieve a use of the inhaler device in compliance with a predefined treatment regimen, which is defined by predefined data. Preferably, the predefined data is patient specific and may be defined by a physician under consideration by amongst others the severity of the disease and the constitution of the patient.

In an embodiment of the present invention the method is further characterized by considering the impact of adaptations of the instructions in timing and/or content on the individual use of the inhaler device when autonomously adapting the timing and/or the content of the instructions. An algorithm of artificial intelligence (AI) may be used to evaluate the impact of single adaptations to the instructions as well as to consider the impact of adaptations when instructing the patient during a subsequent use of the inhaler device.

BRIEF DESCRIPTION OF THE DRAWINGS

The invention will now be described in connection with one exemplary embodiment shown in the Figures in which.

DETAILED DESCRIPTION

Figure 1:
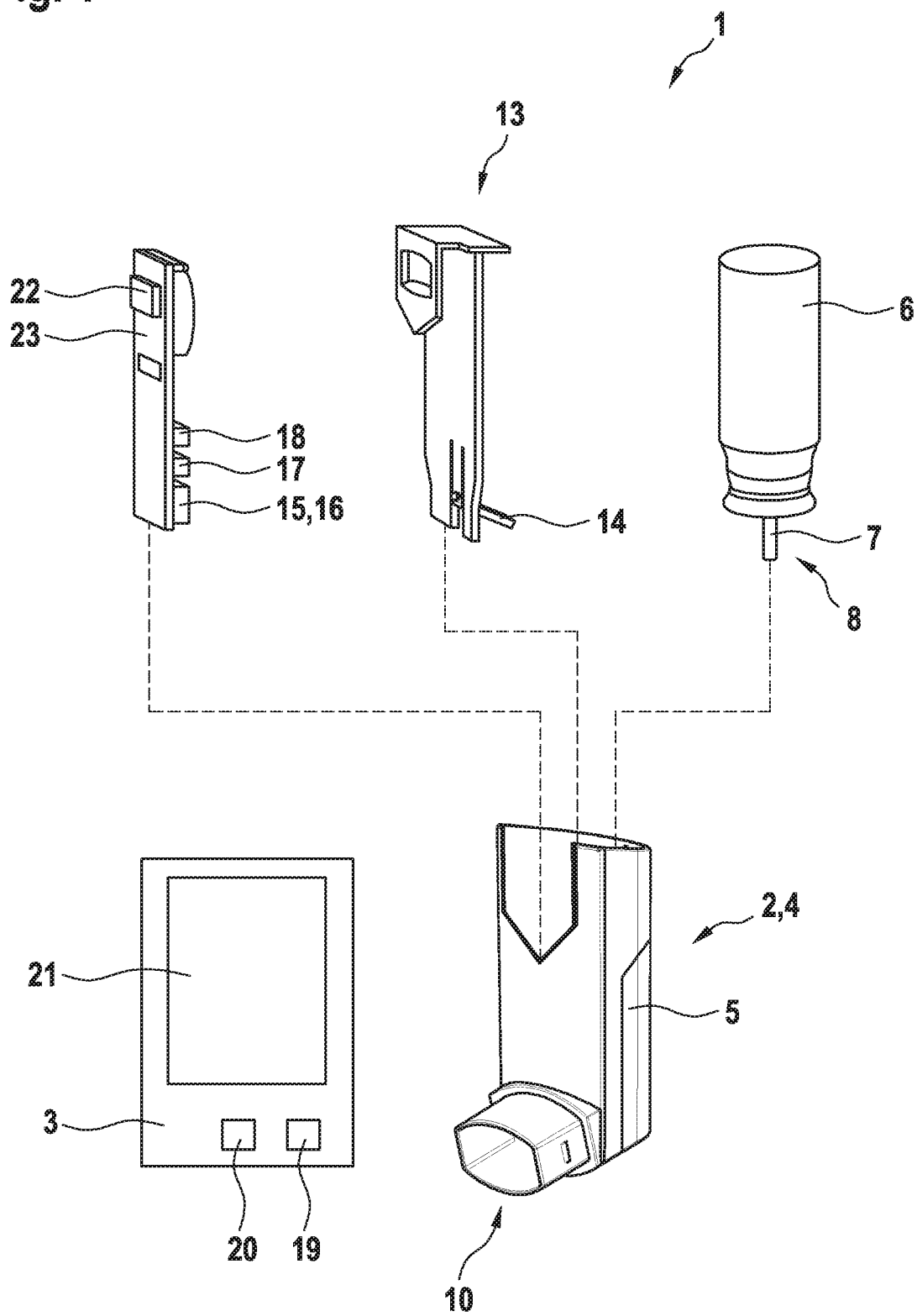
FIG. 1 shows a schematic view of an electronic system according to the present invention with an inhaler device and FIG. 2 shows a cross-sectional view of the inhaler device of FIG. 1.
Figure 2:
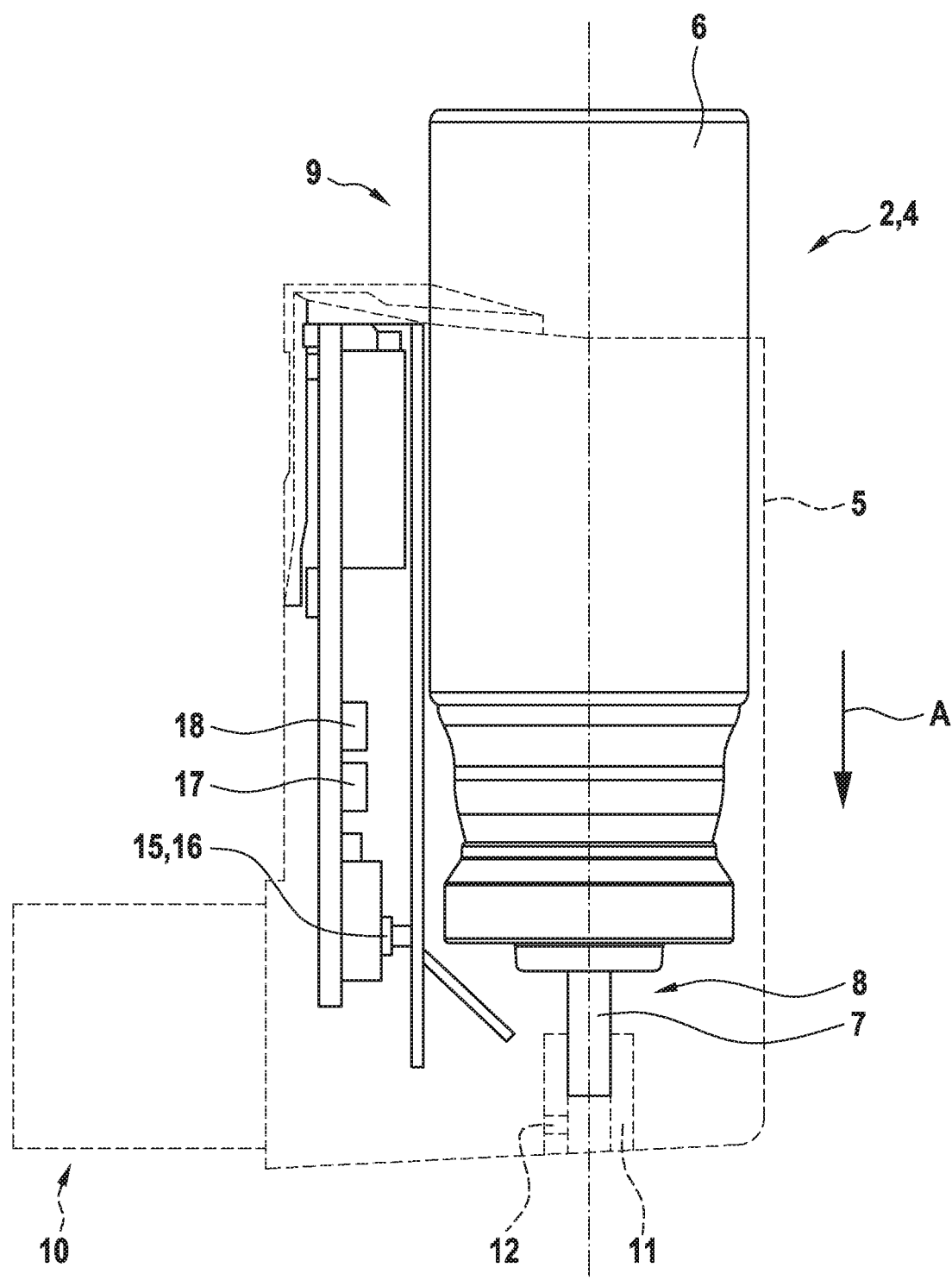

FIGS. 1 and 2 show an electronic system 1 comprising an inhaler device 2 for dispensing a medicament formulation in aerosol form and an external device 3 which is formed as a smart phone, tablet, laptop or any other hand held device. The external device 3 is configured to receive data communicated from the inhaler device 2.

The inhaler device 2 is a metered dose inhaler 4 with a hollow inhaler body 5 for retaining an aerosol container 6 with a dispensing valve 7 at a valve end 8 of the container 6. The inhaler body 5 comprises a first open end 9 sized and arranged to receive the aerosol container 6 with the dispensing valve 7 and a second open end formed as a mouth piece 10 through which a dose of a medicament is dispensed as an aerosol. The mouthpiece 10 is sized and arranged to be coupled to the mouth of a patient (not shown). The inhaler body 5 forms an angular hollow tubular body extending from the first open end 9 towards the mouthpiece 10.

The container 6 is configured to move upon actuation of the metered dose inhaler 4 in the inhaler body 5 in a longitudinal direction A from a rest position to an activation position. In the activation position the valve 7 is depressed against a nozzle block 11 of the inhaler body 5 such that an aerosol dose is released from the aerosol container 6 and streams through a dispensing channel 12 of the nozzle block 11 towards the mouthpiece 10. In connection with the present invention the term actuation of the metered dose inhaler 4 is understood as the depression of the aerosol container 6 from the rest position to the activation position.

The inhaler body 5 includes a triggering unit 13 that is inserted into the first open end 9 of the inhaler body 5. The triggering unit 13 comprises a flexible tongue 14 which is configured to interact with the container 6 such that the flexible tongue 14 is displaced transversally to the longitudinal direction A when the container 6 moves in the longitudinal direction A from the rest position to the activation position.

The metered dose inhaler 4 has an actuation sensing device 15 which comprises at least one actuation sensor that is formed as a switch 16. The switch 16 is configured to sense the actuation of the metered dose inhaler 4 in order to dispense the medicament formulation. Upon actuation of the metered dose inhaler 4, which is the depression of the aerosol container 6 from the rest position to the activation position, the container displaces the flexible tongue 14 such that the flexible tongue 14 triggers the switch 16. Upon being triggered the switch 16 senses an actuation of the metered dose inhaler 4.

The actuation sensing device 15 may comprise additional sensors (not shown), such as a cap detection sensor in order to sense for example the presence of a mouthpiece cap covering the mouthpiece 10 or being removed therefrom.

These additional sensors may be configured to sense preparatory steps of the metered dose inhaler 4 in order to prepare a use of the inhaler 4.

The metered dose inhaler 4 further comprises a flow rate sensor 17 for sensing a flow rate of an inhalation flow which is caused by a patient upon inhalation through the mouthpiece 10 and in which the medicament formulation is dispensed. The flow rate sensor 17 and the switch 16 are configured to generate sensor signals.

The metered dose inhaler 4 further comprises a wireless transmitting unit 18 for communicating data (referred to hereinafter as communicated data) related to the sensor signals to the external device 3. The transmitting unit 18, the switch 16 and the flow rate sensor 17 are positioned on a substrate 23 such as a printed circuit board arranged in the inhaler body 5.

The electronic system 1 further comprises an instruction unit 19 configured to generate visual, tactile and/or acoustic instructions in order to support the patient during use of the metered dose inhaler 4. The instructing unit 19 is arranged on the external device 3. The external device 3 comprises a display 21 on which visual instructions may be shown, a vibration unit (not shown) for communicating tactile instructions and speakers (not shown) through which acoustic instructions are outputted. Alternatively the instruction unit 19 may be arranged in the inhaler body 5 of the metered dose inhaler 4. An inhaler display 22 of the metered dose inhaler 4 may be used to output visual instructions. The metered dose inhaler 4 may also comprise a vibration unit and/or speakers (not shown) by use of which tactile and acoustic instructions may be outputted, respectively.

The instruction unit 19 is configured to generate instructions in the form of visual, tactile and/or acoustic messages in order to guide the patient through the steps of starting inhalation, moving the aerosol container 6 from the rest position into the activation position and holding breath for a predefined period of time subsequent to inhalation.

The electronic system 1 further comprises an evaluation unit 20 for evaluating the communicated data which has been communicated by the transmitting unit 18 from the metered dose inhaler 4 to the external device 3. The evaluation unit 20 is located on the external device 3 or is connectable thereto and may comprise a processor (not shown) for processing the communicated data. The electronic system 1 may comprise a server (not shown) which is wirelessly accessible by the metered dose inhaler 4 and/or the external device 3 and on which alternatively the evaluation unit 20 is stored.

The evaluation unit 20 is configured to evaluate the use of the metered dose inhaler 4 by comparing measurements taken by the sensors 16, 17 with the instructions given to the patient and/or with predefined data. In particular, the evaluation unit is configured to evaluate the use of the metered dose inhaler 4 by comparing the timing of the measurements taken by the sensors 16, 17 with the timing of the instructions given to the patient and/or with predefined data.

The predefined data may for example comprise data relating to the duration of inhalation by the patient, the flow rate of the inhalation flow, the timing of an actuation, in particular a depression, of the aerosol container 6 of the metered dose inhaler 4, the time difference between the start of the inhalation flow upon inhalation by the patient and the actuation of the aerosol container and/or the duration of a depression of an aerosol container 6. The predefined data may be individually defined for each patient by a physician under consideration amongst others of the severity of the disease and the constitution of the patient.

The evaluation unit 20 is further configured to autonomously adapt the timing and/or the content of the instructions in order to ensure that the measurements taken by the sensors 16, 17 correspond to a use of the metered dose inhaler 4 by the patient according to the predefined data. If, for example the time difference between the start of the inhalation flow upon inhalation by the patient and the actuation of the aerosol container 6 is too small, the evaluation unit 20 may adapt the timing of an instruction which instructs the patient to start inhaling such that the instruction unit 19 outputs the corresponding instruction at an earlier point of time compared to a previous use of the metered dose inhaler 4.

Moreover the evaluation unit 20 is configured to verify whether the adaptation of the timing and/or the content of the instructions leads to a use of the metered dose inhaler 4 by the patient according to the predefined data during a subsequent use of the metered dose inhaler 4 by comparing measurements taken by the sensors 16, 17 during the subsequent use of the metered dose inhaler 4 with the predefined data.

Additionally, the evaluation unit 20 is further configured to evaluate how single adaptations of the instructions in timing and/or content impact on the individual use of the metered dose inhaler 4 by the patient by comparing measurements taken by the sensors 16, 17 during the subsequent use of the metered dose inhaler 4 with measurements taken from the sensors 16, 17 during the previous use of the metered dose inhaler 4.

The evaluation unit 20 is further configured to consider the impact of adaptations of the instructions in timing and/or content on the individual use of the metered dose inhaler 4 when autonomously adapting the timing and/or the content of the instructions. The evaluation unit 20 is configured to use an algorithm of artificial intelligence which is capable of evaluating the multiple adaptations with regard to their impact on the use of the metered dose inhaler 4 by the patient. Preferably, the algorithm is capable of arranging the multiple adaptations in an order according to their impact.

Moreover, the evaluation unit 20 is further configured to evaluate how single adaptations to the instructions in timing and/or content impact on the use of the metered dose inhaler 4 based on an evaluation of data generated by further patients using other inhaler devices such as metered dose inhaler, dry powder inhaler or soft mist inhaler and to consider the impact on the use of the metered dose inhaler 4 when autonomously adapting the timing and/or the content of the instructions.

The metered dose inhaler 4 may comprise a first mechanism for adapting a flow cross-section of the inhalation flow (not shown). The first mechanism may be formed as a movable flap which is configured to increase or decrease the flow cross-section of the inhalation flow. The inhaler body 5 may optionally comprise a top cover (not shown) which is located on the first open end 9 of the inhaler body 5 in order to ensure that no air is drawn into the inhaler body 5 through the first open end 9. In this case the inhaler body 5 may comprise an air inlet duct (not shown), preferably located on a backside of the inhaler body 5, opposite the mouthpiece 10, through which upon inhalation by the patient air is drawn into the inhaler body 5. The flap may be arranged in the air inlet duct and may be rotatable within the air inlet duct around an axis of rotation.

Additionally or alternatively the metered dose inhaler 4 may comprise a second mechanism for adapting a flow cross-section of the dispensing channel 12 of the nozzle block 11 of the metered dose inhaler 4 through which the medicament formulation is dispensed towards the mouthpiece 10 and into the inhalation flow. The second mechanism may be formed as multiple segments (not shown) positioned transversally to a longitudinal axis of the dispensing channel 12 and being configured to be driven radially inward into or outward of the dispensing channel 12 in order to decrease or increase the flow cross-section of the dispensing channel 12.

The evaluation unit 20 may further be configured to control the first and/or the second mechanism of the metered dose inhaler 4. The evaluation unit 20 may be connected to the flap such that the flap is automatically rotatable upon request by the evaluation unit 20. Moreover, the evaluation unit 20 may be connected to the second mechanism in order to control the second mechanism upon request.

In the following a method for controlling an electronic system 1 is described with reference to FIGS. 1 and 2.

In a first step the electronic system 1 as described above is provided, wherein the inhaler device is a metered dose inhaler 4.

In a second step the use of the metered dose inhaler 4 is evaluated by comparing measurements taken by the sensors 16, 17 with the instructions given to the patient and/or with predefined data. In particular, the timing of the measurements is compared to the timing of the instructions.

In case the result of the evaluation is that the measurements taken by the sensors 16, 17 do not essentially correspond with the instructions given to the patient and/or with predefined data a third method step is taken. In the third step the timing and/or the content of the instructions is autonomously adapted. The aim of the adaptation is to achieve that the measurements taken by the sensors correspond to a use of the inhaler device by the patient according to the predefined data. The instructions are adapted by the evaluation unit 20 and outputted in a subsequent use of the metered dose inhaler 4 by the instruction unit 19. Additionally, the evaluation unit 20 may request the first and second mechanism to adapt a flow cross-section of the inhalation flow and/or a flow cross-section of the dispensing channel 12 of the metered dose inhaler 4 through which the medicament formulation is dispensed into the inhalation flow.

In a fourth step it is verified whether the adaptation of the timing and/or the content of the instructions leads to a use of the metered dose inhaler 4 by the patient according to the predefined data during a subsequent use of the metered dose inhaler 4 by comparing measurements taken by the sensors 16, 17 during the subsequent use of the metered does inhaler 4 with the predefined data.

In a fifth step it is evaluated how single adaptations of the instructions in timing and/or content impact on the individual use of the metered dose inhaler 4 by the patient by comparing measurements taken by the sensors 16, 17 during the subsequent use of the metered dose inhaler 4 with measurements taken from the sensors 16, 17 during the previous use of the metered dose inhaler 4.

The evaluation unit 20 considers the impact of adaptations of the instructions in timing and/or content on the individual use of the metered dose inhaler 4 when autonomously adapting the instructions for a subsequent use of the metered dose inhaler 4.

The steps three to five are repeated in subsequent uses until the measurements taken by the sensors 16, 17 essentially correspond to a use of the metered dose inhaler 4 by the patient according to the predefined data. In connection with the present invention the term essentially correspond is understood in such a way that the measurements do not have to be identical with the predefined data but have to lie within a defined tolerance field of the values of the predefined data.

REFERENCE NUMERALS 1 electronic system
2 inhaler device
3 external device
4 metered dose inhaler
5 inhaler body
6 aerosol container
7 dispensing valve
8 valve end
9 first open end
10 mouthpiece (second open end)
11 nozzle block
12 dispensing channel
13 triggering unit
14 flexible tongue
15 actuation sensing device
16 switch (actuation sensor)
17 flow rate sensor
18 transmitting unit
19 instruction unit
20 evaluation unit
21 display
22 inhaler display
23 substrate

The invention claimed is:

1. An electronic system comprising:
an inhaler device for dispensing a medicament formulation in aerosol or dry powder form and
an external device which is configured to receive data communicated from the inhaler device,
wherein the inhaler device comprises:
 a mouthpiece,
 a flow rate sensor for sensing a flow rate of an inhalation flow which is caused by a patient upon inhalation through the mouthpiece and in which the medicament formulation is entrained or dispensed,
 an actuation sensing device having at least one actuation sensor which is configured to sense preparatory steps of the inhaler device in order to prepare a use of the inhaler device and/or to sense the actuation of the inhaler device in order to dispense the medicament formulation, the at least one actuation sensor and the flow rate sensor being configured to generate sensor signals and
 a wireless transmitting unit for communicating data related to the sensor signals to the external device,
wherein the electronic system further comprises:
an instruction unit configured to generate visual, tactile and/or acoustic instructions in order to support the patient during use of the inhaler device and
an evaluation unit for evaluating the sensor signals and/or the communicated data, the evaluation unit being configured to:
evaluate a use of the inhaler device by comparing measurements taken by the sensors with the instructions given to the patient and/or with predefined data,
wherein
the evaluation unit is further configured to:
autonomously adapt the point in time at which the instructions are outputted in order to ensure that the measurements taken by the sensors correspond to a use of the inhaler device by the patient according to the predefined data,
verify whether an adaptation of timing of the instructions leads to a use of the inhaler device by the patient according to the predefined data during a subsequent use of the inhaler device by comparing measurements taken by the sensors during the subsequent use of the inhaler device with the predefined data and evaluate how single adaptations of the instructions in timing impact on individual use of the inhaler device by the patient by comparing measurements taken by the sensors during the subsequent use of the inhaler device with measurements taken from the sensors during the previous use of the inhaler device.

2. The electronic system according to claim 1 wherein the evaluation unit is further configured to consider an impact of adaptations of the instructions in timing on the individual use of the inhaler device when autonomously adapting the timing and/or the content of the instructions.

3. The electronic system according to claim 1, wherein the evaluation unit is further configured to evaluate how single adaptations to the instructions in timing impact on the use of the inhaler device based on an evaluation of data generated by further patients using other inhaler devices and to consider an impact on the use of the inhaler device when autonomously adapting the timing of the instructions.

4. The electronic system according to claim 1, wherein the predefined data comprises data relating to a duration of inhalation by the patient, a flow rate of the inhalation flow, a timing of an actuation, of an aerosol container of the inhaler device, a time difference between the start of the inhalation flow upon inhalation by the patient and an actuation of the aerosol container and/or a duration of a depression of an aerosol container.

5. The electronic system according to claim 4, wherein the timing of an actuation is a depression.

6. The electronic system according to claim 1, wherein the inhaler device comprises a mechanism for adapting a flow cross-section of the inhalation flow and/or a flow cross-section of a dispensing channel of the inhaler device through which the medicament formulation is dispensed into the inhalation flow.

7. The electronic system according to claim 6 wherein the mechanism is formed as a movable flap which is configured to increase or decrease the flow cross-section of the inhalation flow.

8. The electronic system according to claim 6 wherein the mechanism is formed as multiple segments positioned transversally to a longitudinal axis of the dispensing channel and being configured to be driven radially inward into or outward of the dispensing channel in order to decrease or increase the flow cross-section of the dispensing channel, respectively.

9. The electronic system according to claim 6 wherein the evaluation unit is further configured to control the mechanism of the inhaler device.

10. The electronic system according to claim 1, wherein the evaluation unit is further configured to evaluate the use of the inhaler device by comparing the measurements taken by the sensors regarding their timing with the instructions given to the patient regarding their timing and/or with predefined data.

11. The electronic system according to claim 1, wherein the inhaler device is a metered dose inhaler, a dry powder inhaler or a soft mist inhaler.

12. The electronic system according to claim 1, wherein the external device comprises the evaluation unit or is connectable thereto.

13. The electronic system according to claim 1, wherein the electronic system comprises a server which is wirelessly accessible by the inhaler device and/or the external device and on which the evaluation unit is stored.

14. A method for controlling an electronic system, comprising the steps of:
 a) providing an electronic system according to claim 1,
 b) evaluating the use of the inhaler device by comparing measurements taken by the sensors with the instructions given to the patient and/or with predefined data,
 c) autonomously adapting the timing of the instructions in order to ensure that the measurements taken by the sensors correspond to a use of the inhaler device by the patient according to the predefined data,
 d) verifying whether the adaptation of the timing of the instructions leads to a use of the inhaler device by the patient according to the predefined data during a subsequent use of the inhaler device by comparing measurements taken by the sensors during the subsequent use of the inhaler device with the predefined data and
 e) evaluating how single adaptations of the instructions in timing impact on the individual use of the inhaler device by the patient by comparing measurements taken by the sensors during the subsequent use of the inhaler device with measurements taken from the sensors during the previous use of the inhaler device.

15. The method according to claim 14, further comprising considering an impact of adaptations of the instructions in timing and/or content on the individual use of the inhaler device when autonomously adapting the timing of the instructions.

16. The method according to claim 14, further comprising repeating steps c) to e) in subsequent uses until the measurements taken by the sensors correspond to a use of the inhaler device by the patient according to the predefined data.

17. The method according to claim 15, further comprising repeating steps c) to e) in subsequent uses until the measurements taken by the sensors correspond to a use of the inhaler device by the patient according to the predefined data.

* * * * *